(12) United States Patent
Lee et al.

(10) Patent No.: US 10,918,598 B2
(45) Date of Patent: Feb. 16, 2021

(54) ON DEMAND VESICLE FORMATION FROM VESICLE PRECURSORS SUITABLE FOR LONG-TERM STORAGE

(71) Applicant: The Regents of the University of California, Oakland, CA (US)

(72) Inventors: Abraham P. Lee, Irvine, CA (US); Derek Vellejo, Chino, CA (US); Crystal Rapier, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 234 days.

(21) Appl. No.: 14/964,381

(22) Filed: Dec. 9, 2015

(65) Prior Publication Data

US 2016/0158151 A1 Jun. 9, 2016

Related U.S. Application Data

(60) Provisional application No. 62/089,773, filed on Dec. 9, 2014.

(51) Int. Cl.
| | | |
|---|---|---|
| *A61K 39/395* | (2006.01) | |
| *A61K 9/113* | (2006.01) | |
| *A61K 39/00* | (2006.01) | |
| *A61K 9/127* | (2006.01) | |

(52) U.S. Cl.
CPC .............. *A61K 9/113* (2013.01); *A61K 9/127* (2013.01); *A61K 9/1277* (2013.01); *A61K 39/00* (2013.01); *A61K 2039/55566* (2013.01); *A61K 2039/605* (2013.01)

(58) Field of Classification Search
None
See application file for complete search history.

(56) References Cited

U.S. PATENT DOCUMENTS

| | | | | |
|---|---|---|---|---|
| 2005/0266066 | A1* | 12/2005 | Uchida | A61K 9/1271 424/450 |
| 2006/0188463 | A1* | 8/2006 | Kim | A61K 8/066 424/70.13 |
| 2011/0150953 | A1* | 6/2011 | Ichikawa | A61K 8/14 424/401 |

OTHER PUBLICATIONS

Qi et al, J of Pharmaceutical Sciences, 2011, vol. 100, No. 6, p. 2203-2211.*
Kanouni et al. Advances in Colloid and Interface Science, vol. 99, pp. 229-254, 2002.*
Arriaga, et al. 2013 "Ultrathin Shell Double Emulsion Templated Giant Unilamellar Lipid Vesicles with Controlled Microdomain Formation" *Small* 10(5): 950-956.
Dao, et al. 1991 "Large-scale preparation of asymmetrically labeled fluorescent lipid vesicles" *Analytical Biochemistry* 196: 46-53.
Dos Santos, et al. 2010 "Surface Tensions, Surface Potentials, and the Hofmeister Series of Electrolyte Solutions" *Langmuir* 26(13): 10778-10783.
Dos Santos, et al. 2012 "Surface and interfacial tensions of Hofmeister electrolytes" *Faraday Discussions* 160: 75-87.
Hayward, et al. 2006 "Dewetting Instability during the Formation of Polymersomes from Block-Copolymer-Stabilized Double Emulsions" *Letters* 22(10): 4457-4461.
Lima, et al. 2013 "Specific Ion effects on the interfacial tension of water/hydrocarbon systems" *Brazilian Journal of Chemical Engineering* 30(01): 55-62.
Lorenceau, et al. 2005 "Generation of Polymerosomes from Double-Emulsions" *Langmuir* 21: 9183-9186.
Moscho, et al. 1996 "Rapid preparation of giant unilamellar vesicles" *Proc. Natl. Acad. Sci.* 93: 11443-11447.
Ota, et al. 2009 "Microfluidic Formation of Monodisperse, Cell-Sized, and Unilamellar Vesicles" *Angew Chem. Int. Ed.* 46: 6533-6537.
Rodriguez, et al. 2005 "Giant vesicles formed by gentle hydration and electroformation: A comparison by fluorescence microscopy" *Colloids and Surfaces B; Biointerfaces* 42: 125-130.
Shum, et al. 2008 "Double Emulsion Templated Monodisperse Phospholipid Vesicles" *Langmuir* 24: 7651-7653.
Shum, et al. 2011 "Multicompartment Polymersomes from Double Emulsions" *Angew Chem. Int. Ed* 50: 1648-1651.
Stachowiak, et al. 2008 "Unilamellar vesicle formation and encapsulation by microfluidic jetting" *PNAS* 105(12): 4697-4702.
Stachowiak, et al. 2009 "Inkjet formation of unilamellar lipid vesicles for cell-like encapsulation" *Lab Chip* 9(14): in 14 pages.
Stark, et al. 2010 "Long-term stability of sterically stabilized liposomes by freezing and freeze-drying: Effects of cryoprotectants on structure" *European Journal of Pharmaceutical Sciences* 41: 546-555.
Tamba, et al. 2004 "Stability of giant unilamellar vesicles and large unilamellar vesicles of liquid-ordered phase membranes in the presence of Triton X-100" *Biochimica et Biophysica Acta* 1667: 1-6.
Teh 2010 "Lab on a Chip/Art in Science and MicroTAS 2009 Nov. 1-5, 2009, Jeju, Korea" *Lab Chip* 10: 681-682.

(Continued)

*Primary Examiner* — Yunsoo Kim
(74) *Attorney, Agent, or Firm* — Knobbe, Martens, Olson & Bear, LLP

(57) ABSTRACT

Disclosed is a water-in-oil-in-water (W/O/W) double emulsion including a first water phase, an oil phase and a second water phase, wherein the W/O/W double emulsion is disposed in an isotonic solution, and related methods of making the W/O/W double emulsion. Also disclosed is a method of making an artificial antigen presenting cell including: providing a W/O/W double emulsion that is stored in an isotonic solution, wherein the W/O/W double emulsion includes a peptide associated with a Major Histocompatibility (pMHC) complex or a glycolipid antigen associated with a CD1d molecule, and a costimulatory molecule; and transferring the W/O/W double emulsion to an electrolyte solution, wherein the double emulsion undergoes a morphological transformation to become the artificial antigen presenting cell. Also disclosed is a method of drug delivery including administering to a subject a unilamellar vesicle containing the drug. Other methods relate to storing a protein including making a water-in-oil-in-water (W/O/W) double emulsion, wherein the W/O/W double emulsion includes the protein, and wherein the W/O/W double emulsion is configured to be stably stored.

15 Claims, 8 Drawing Sheets

(56) References Cited

OTHER PUBLICATIONS

Teh, 2011 "Stable, biocompatible lipid vesicle generation by solvent extraction-based droplet microfluidics" *Biomicrofluidics* 5: pp. 1-12.
Walde, et al. 2010 "Giant Vesicles: Preparations and Applications" *ChemBioChem* 11: 848-865.
Yoshitani, et al. 2008 "Water permeability of lipid membranes of GUVs and its dependence on actin cytoskeletons inside the GUVs" pp. 130-134.

* cited by examiner

A)

B)

ON DEMAND VESICLE FORMATION FROM VESICLE PRECURSORS SUITABLE FOR LONG-TERM STORAGE

STATEMENT REGARDING FEDERALLY SPONSORED R&D

This invention was made with government support under funds awarded by The National Institutes of Health (R01-EB012058). The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

Methods of making a water-in-oil-in-water (W/O/W) double emulsion and of making vesicles from a W/O/W double emulsion are provided, as are W/O/W double emulsion compositions and long term stable vesicle precursor compositions.

Description of the Related Art

Methods to make giant unilamellar vesicles (GUVs) in bulk solution are widespread (H. N. T. Dao et al. 1991 *Analytical Biochemistry* 196: 46-53; A. Moscho et al. 1996 *Proc Natl Acad Sci USA* 93: 11443-11447; N. Rodriguez et al. 2005 *Colloids and Surfaces B: Biointerfaces* 42: 125-130; and P. Walde et al. 2010 *Chembiochem* 11: 848-865), but suffer from high polydispersity, multilamellar membranes, and low encapsulation efficiency. Microfluidic methods to form GUVs have overcome these limitations, but are generally limited to two methodologies: forming GUVs from the microfluidic jetting of a preformed lipid bilayer (S. Ota et al. 2009 *Angewandte Chemie-International Edition* 48: 6533-6537; J. C. Stachowiak et al. 2008 *Proc Natl Acad Sci USA* 105: 4697-4702; J. C. Stachowiak et al. 2009 *Lab on a Chip* 9: 2003-2009), or utilizing some form of post-processing to convert double emulsion templates into vesicles (H. C. Shum et al. 2008 *Langmuir* 24: 7651-7653; L. R. Arriaga et al. 2013 *Small*, pages 950-956; S.-Y. The et al. 2011 *Biomicrofluidics* 5: 044113-044113-12).

To form the bilayer used for microfluidic jetting, lipids are dissolved in an "oil" phase that is then placed between two aqueous compartments where it can thin and form a bilayer at a central region. Applying a focused pressure to one side of the bilayer forces the bilayer to expand and eventually break off and encapsulate a portion of fluid. This process then repeats multiple times per second to allow for continuous vesicle production. The shortcomings of this method stem from the fact that specialized training is required to form the bilayer, the supply of lipids to make vesicles is limited to those initially present in the preformed planar bilayer, the oils used tend to be volatile and non-biocompatible which can cause problems when encapsulating biological components, and fine pressure control is needed as fluctuations may cause the fragile planar bilayer to break.

The use of double emulsion templates to make lipid vesicles is also widely popular, and is accomplished by co-flowing two immiscible fluid phases: an internal aqueous phase and a surrounding sheath (or "oil") phase composed of either an organic solvent or non-volatile oil, with dissolved lipids. Both phases are sheared together by an external aqueous phase to produce a double emulsion (FIG. 1.). Most methods for forming vesicles from these double emulsions involve using a volatile organic solvent as the "oil" phase. Shortly after production, the volatile solvent begins to evaporate out of solution. As the shell of organic volatile solvent gets thinner, a depletion force will arise that causes the lipids to form a bilayer, and the solvent to retract to one side of the emulsion in a process known as "dewetting" (R. C. Hayward et al. 2006 *Langmuir* 22: 4457-4461). The volatile solvent will eventually evaporate, leaving behind a lipid vesicle. The vesicles can also be formed by solvent extraction of a non-volatile oil phase when evaporation is not possible (S. Y. Teh and A. P. Lee, "Microfluidic double emulsions for the formulation of lipid vesicles and the controlled encapsulation of cells," presented at the 13th International Conference on Miniaturized Systems for Chemistry and Life Sciences (MicroTAS 2009), Jeju, Korea, 2009). Contrary to the former method, the oil phase is composed of a fatty acid/lipid mixture. The fatty acid is slightly soluble in alcohols, so a small percentage of ethanol in the external solution will extract the fatty acid from the bilayer, conceivably allowing a lipid vesicle to form within 15 hours (FIG. 2).

Unfortunately, vesicles have a short life span in solution and begin to degrade via hydrolysis or oxidation of the lipid bilayer (Y. Tamba et al. 2004 *Biochimica Et Biophysica Acta-Biomembranes* 1667: 1-6; B. Stark et al. 2010 *Eur J Pharm Sci* 41: 546-55). Nearly all the work to improve vesicle shelf life focuses on modifying some condition of the vesicles after they have been produced (such as freeze drying (B. Stark et al. 2010 *Eur J Pharm Sci* 41: 546-55)), where the reversal of this process can be damaging to the vesicle population. To make vesicles suitable for widespread use in clinical and commercial settings, it is tantamount that they can be produced in bulk, and stored for a reasonable amount of time without degradation or alteration to their structure.

SUMMARY OF THE INVENTION

Some embodiments relate to a water-in-oil-in-water (W/O/W) double emulsion comprising a first water phase, an oil phase and a second water phase, wherein the W/O/W double emulsion is in an isotonic solution.

In some embodiments, the oil phase comprises a polar lipid.

In some embodiments, the isotonic solution comprises a surfactant.

In some embodiments, the surfactant is a nonionic surfactant.

In some embodiments, the surfactant is an amphoteric surfactant.

In some embodiments, the polar lipid is a zwitterionic lipid.

In some embodiments, the polar lipid is a phospholipid.

In some embodiments, the phospholipid is a natural phospholipid.

In some embodiments, the phospholipid is a synthetic phospholipid.

In some embodiments, the phospholipid is selected from the group consisting of phosphatidic acid (phosphatidate) (PA), phosphatidylethanolamine (cephalin) (PE), phosphatidylcholine (lecithin) (PC), phosphatidylserine (PS), phosphatidylinositol (PI), phosphatidylinositol phosphate (PIP), phosphatidylinositol bisphosphate (PIP2), phosphatidylinositol triphosphate (PIP3), dimyristoylphosphatidylcholine, ceramide phosphorylcholine (Sphingomyelin) (SPH), ceramide phosphorylethanolamine (Sphingomyelin) (Cer-PE) and ceramide phosphoryllipid.

In some embodiments, the oil phase further comprises a cholesterol molecule.

In some embodiments, the W/O/W double emulsion further includes an agent selected from the group consisting of a drug, a fluorescent molecule, an amino acid, a protein, a peptide, a nucleic acid, a DNA molecule or an RNA molecule.

Other embodiments relate to a method of making a water-in-oil-in-water (W/O/W) double emulsion comprising:
    forming a water-in-oil-in-water (W/O/W) double emulsion, wherein the W/O/W double emulsion comprises a first water phase, an oil phase and a second water phase, wherein the oil phase (O) comprises a polar lipid; and
    storing the W/O/W double emulsion in an isotonic solution.

Other embodiments relate to a method of producing a unilamellar vesicle comprising:
    providing a W/O/W double emulsion that is stored in an isotonic solution; and
    transferring the W/O/W double emulsion to an electrolyte solution, wherein the double emulsion undergoes a morphological transformation to become the unilamellar vesicle.

In some embodiments, the unilamellar vesicle is a giant unilamellar vesicle (GUV).

In some embodiments, the unilamellar vesicle comprises an agent contained within a lipid bilayer, wherein the agent is selected from the group consisting of a drug, a fluorescent molecule, an amino acid, a protein, a peptide, a nucleic acid, a DNA molecule and an RNA molecule.

In some embodiments, the lipid bilayer of the unilamellar vesicle contains one or more protein molecules embedded in the lipid bilayer.

In some embodiments, an oil cap is removed from the unilamellar vesicle by applying a high shear flow force.

Some embodiments relate to an method of making an artificial antigen presenting cell comprising:
    providing a W/O/W double emulsion that is stored in an isotonic solution, wherein the W/O/W double emulsion comprises a peptide associated with a Major Histocompatibility (pMHC) complex or a glycolipid antigen associated with a CD1d molecule, and a costimulatory molecule; and
    transferring the W/O/W double emulsion to an electrolyte solution, wherein the double emulsion undergoes a morphological transformation to become the artificial antigen presenting cell.

In some embodiments, the pMHC complex comprises a peptide antigen from a pathogen and a major histocompatibility complex type I and/or a major histocompatibility complex type II molecule.

In some embodiments, a glycolipid antigen is presented by a CD1d molecule.

Some embodiments relate to a method of stimulating a T helper (TH) cell or a cytotoxic T cell (TC) comprising contacting the TH cell or the TC with an artificial antigen presenting cell as disclosed herein.

Some embodiments relate to a method of stimulating a natural killer T Cell (NKT) comprising contacting the NKT cell with an artificial antigen presenting cell, wherein a glycolipid antigen is presented by a CD1d molecule.

Some embodiments relate to a method of drug deliver comprising administering to a subject a unilamellar vesicle containing the drug.

Some embodiments relate to a method of storing a protein comprising making a water-in-oil-in-water (W/O/W) double emulsion, wherein the W/O/W double emulsion comprises the protein, and wherein the W/O/W double emulsion is configured to be able to be stably stored for up to one year or more.

DETAILED DESCRIPTION OF THE PREFERRED EMBODIMENT

Figure 3:
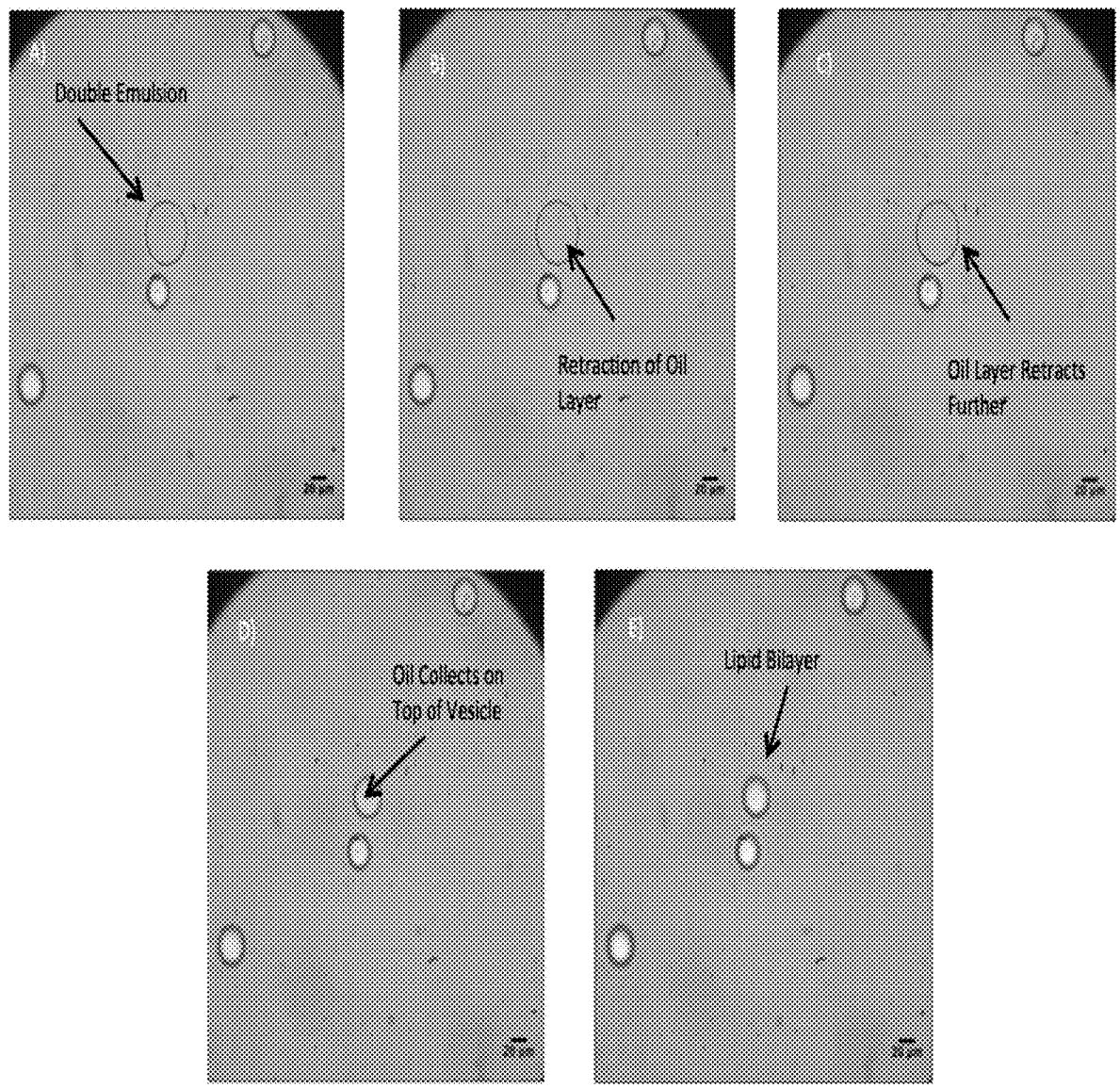
FIG. 3. Time lapse images of dewetting process. A) t=0 ms. B) t=380 ms. C) t=540 ms. D) t=1600 ms. E) t=2400 ms.
Figure 4:
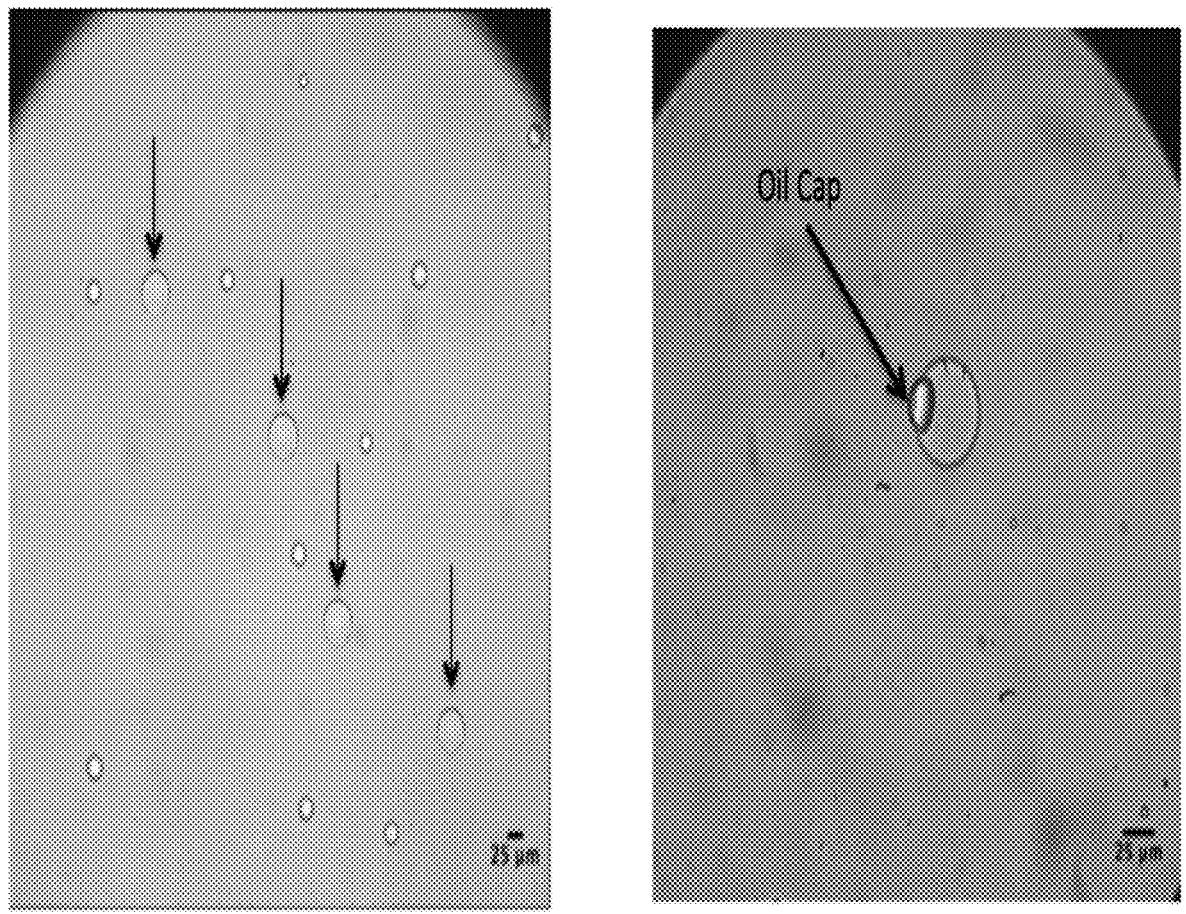
FIG. 4. Left: Cross-sectional view of double emulsions undergoing dewetting. Arrows indicate collection of oil that will form the "cap". The oil layer can be seen to be thinning on the bottom of the double emulsions. Past a critical thickness a depletion force will arise, promoting lipid aggregation and complete dewetting of the oil layer. Right: Cross-sectional view of vesicle with oil cap.
Figure 5:
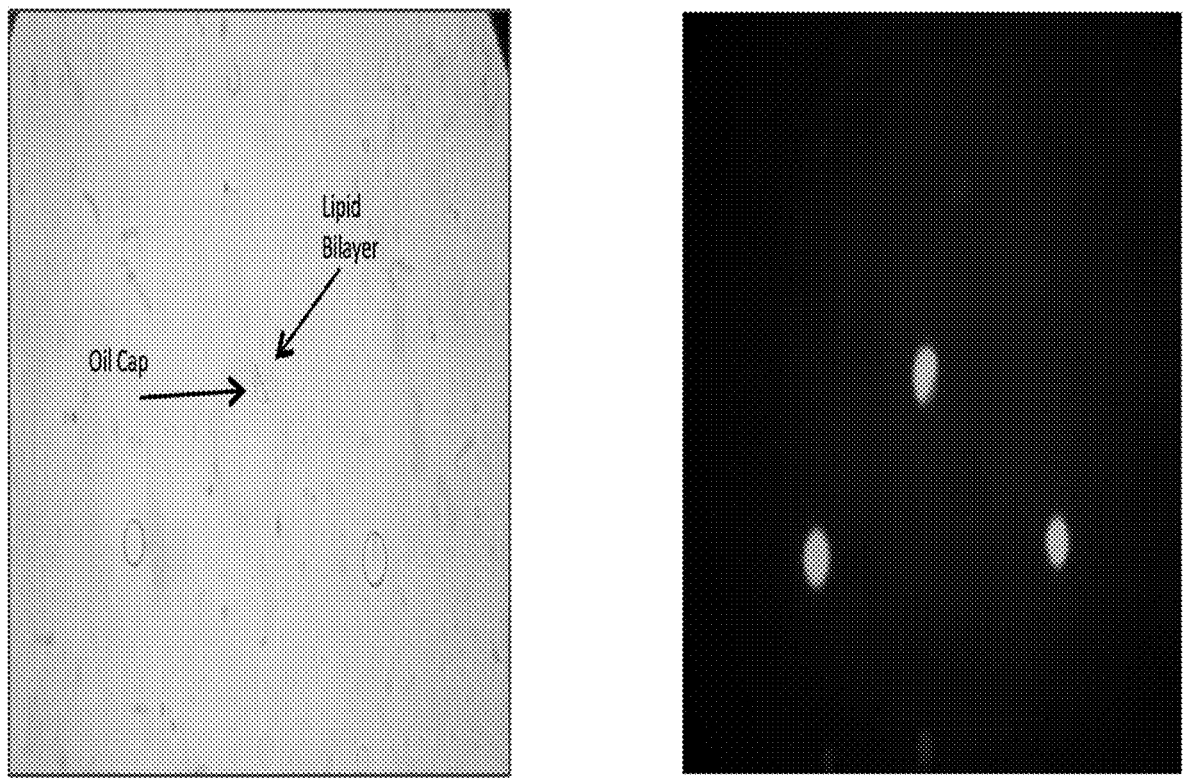
FIG. 5. Optical and fluorescent microscopic images of a vesicle with encapsulated fluorescein labeled dextran. Left: Optical microscope image. Right: Fluorescent image of same vesicle demonstrating successful encapsulation of fluorescein labeled dextran and containment within the bilayer following dewetting.

We have developed a method to circumvent the storage limitations of GUVs, and can form GUVs without the use of harmful volatile solvents. Using a microfluidic device, we make water-in-oil-in-water (W/O/W) double emulsions that can be processed into vesicles at any time post-production. The double emulsions are stored in an isotonic solution with a small amount of surfactant and are stable for over a year. Upon introduction into an electrolyte solution, such as PBS, cell media, serum or blood, the double emulsions will spontaneously form into vesicles within a few minutes by shedding their oil layer. This process is based on inducing an increase in interfacial tension inside and outside of the double emulsion. The ions cause instability at both water-oil interfaces, forcing the oil to minimize its surface area by forming into a "cap" on one region of the double emulsion (FIG. 3). As the oil layer thins, the lipids accumulate into a bilayer, which then forces any remaining oil to retreat and accumulate into the oil "cap" (FIG. 4). Even with the oil cap attached, the amount of exposed bilayer (>80-90% of the surface area) should be sufficient for most applications. In some embodiments, the oil cap is removed. The GUVs can be stored in a precursor form for an extended period of time, making them suitable for commercial applications.

A benefit of the methods disclosed herein are that they are safe for biological applications due to the use of biocompatible oils rather than volatile organic solvents. The methods provide a means by which vesicles are a feasible option for real-world applications beyond the lab bench. They can be mass-produced in precursor form at a central facility, greatly reducing costs as it negates the need for the end user to buy expensive commercial equipment for vesicle production. The consumer can also store the double emulsion precursors for extended periods of time, and functionalize the double emulsions before use as vesicles. Simply placing the double emulsions into an electrolyte solution transforms them into vesicles. No extra steps are needed to ensure the transformation.

Figure 7:
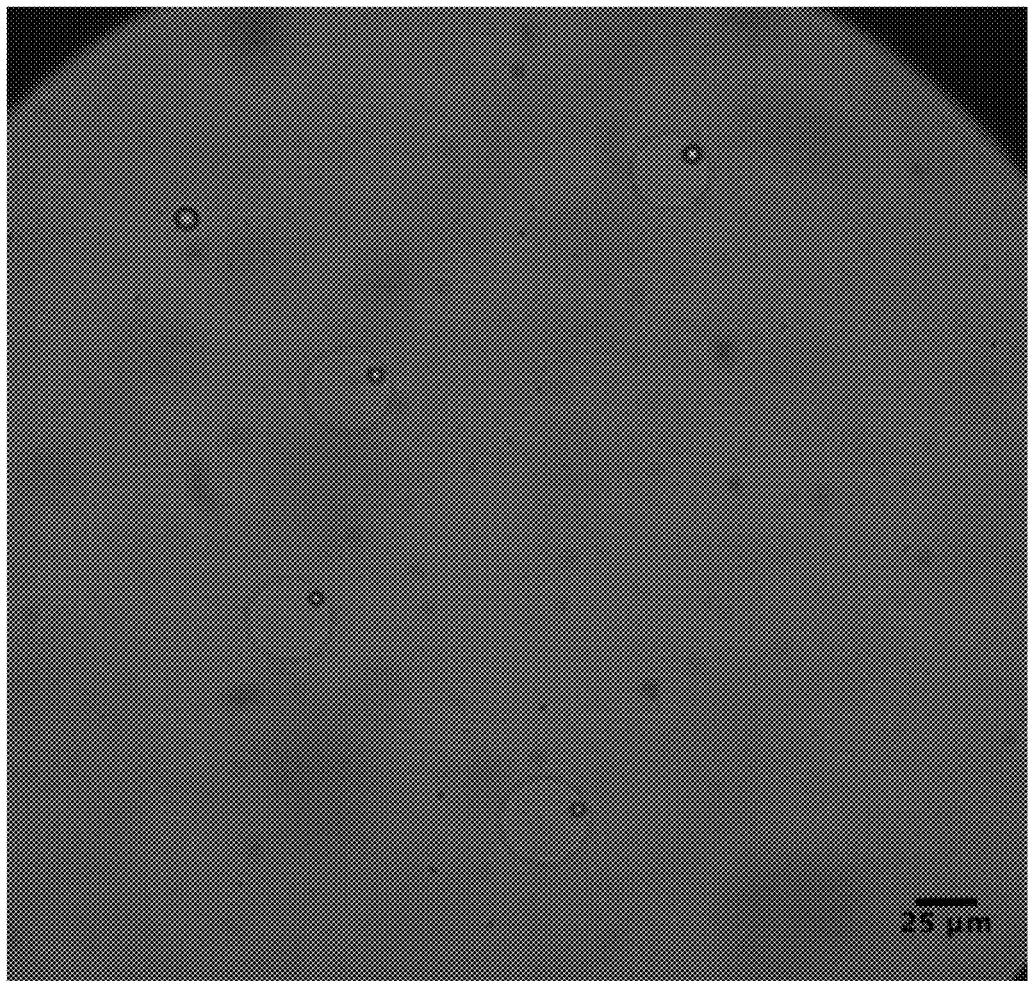
FIG. 7. Vesicles develop very small oil caps when exposed to the iodide ion (I−).

We unexpectedly discovered the phenomenon of vesicle formation from double emulsions when osmotic shock tests were being performed on thin layer double emulsions, which were, at the time, believed to be vesicles. The test required that the concentration of solutes in the external solution be increased to promote water leakage from the double emulsions and cause them to shrink. The rate of shrinkage can be used to estimate the permeability of the oil layer to water. This had traditionally been accomplished by adding sucrose to the external solution. When using NaCl instead of the sucrose, it was noticed that on some occasions, all the vesicles seemed to pop; but upon closer inspection we observed that there was a very thin spherical outline around all the oil droplets in the solution (FIG. 7). Since the thickness of a lipid bilayer is on the order of a few nanometers, it was reasonable that a lipid bilayer should be difficult to see using an optical microscope.

Although another group had witnessed double emulsion dewetting when using volatile solvents in their double emulsion templates, their process is driven by a different mechanism entirely; i.e., the evaporation of the organic solvent (R. C. Hayward et al. 2006 *Langmuir* 22: 4457-4461). Thus, their double emulsions form into vesicles shortly after production regardless of the storage conditions, whereas in our method, we can control precisely when dewetting occurs by exposing the double emulsions to electrolytes. When a volatile organic solvent is used, the solvent shell slowly evaporates and reduces in thickness, promoting a depletion effect. The depletion effect is a process whereby colloidal particles (lipids in this case) in solution that are larger than the solvent molecules tend to be attracted to each other at short distances. Hayward et al. (R. C. Hayward et al. 2006 *Langmuir* 22: 4457-4461) noted that as the solvent from the double emulsions began evaporating, the shell would become increasingly thin, causing the local concentration of polymer to increase. As the particles became more packed in the thinning shell, the depletion force grew stronger, ultimately causing the hydrophobic regions of the polymers to aggregate while pushing away the smaller organic solvent molecules. The organic solvent then collected as a cap on one end of the structure and eventually evaporated. They derived that one variable that was directly related to the strength of the depletion effect was solute concentration.

When we increased the lipid concentration in the oil phase of our double emulsions, we noticed that they would dewet shortly after production, while still in a solution with surfactant, confirming their results. Addition of cholesterol to the oil phase of the double emulsions disrupted the depletions effect and did not allow the double emulsions to dewet, even when moved to a sucrose solution without surfactant. Only when the interfacial tension was increased with the addition of electrolytes did the double emulsions dewet. In our system, an interfacial effect caused dewetting rather than evaporation, as used by Hayward et al. (R. C. Hayward et al. 2006 *Langmuir* 22: 4457-4461). The increase in interfacial tension at the surface of the double emulsions led to a local thinning at one portion of the oil layer, causing the local lipid concentration in that area to also increase, allowing the depletion force to promote dewetting. By changing the interfacial tension, we can precisely control when the dewetting process occurs, whereas other groups cannot (L. R. Arriaga et al. 2013 *Small*, pages 950-956; E. Lorenceau et al. 2005 *Langmuir* 21: 9183-9186; H. C. Shum et al. 2011 *Angewandte Chemie-International Edition* 50: 1648-1651), since volatile solvents always evaporate shortly after double emulsion production, immediately putting vesicles at risk of degradation through hydrolysis and oxidation.

Lipid Bilayers, Vesicles and Encapsulated Constituents

Polar lipids form bilayers spontaneously in water. There are three classes of polar lipids, including zwitterionic, uncharged (glyco-) and anionic lipids. Examples of zwitterionic lipids include phosphatidyl choline (PC), phosphatidyl ethanolamine (PE) and sphingomyelin (SM). Examples of uncharged lipids include glycolipids, cerebrosides and gangliosides. Examples of anionic lipids include P-glycerol (PG), P-inositol (PI), cardiolipin (CI) and P-serine (PS).

A lipid bilayer is a thin polar membrane made of two layers of lipid molecules that can form a bilayer sheet, a liposome or a micelle. A useful characteristic of vesicles is their ability to encapsulate (or perhaps excapsulate) ionic molecules from a surrounding aqueous medium. Thus, the invention includes embodiments wherein a reagent is included in the composition of lipids or lipid-forming materials and/or in the aqueous composition and at least a portion of the reagent is encapsulated (or excapsulated) in a vesicle. Examples of reagents which may be encapsulated in vesicles as part of the above-described methods include small molecules (for example, drugs, fluorescent molecules, amino acids) and large molecules (for example, proteins, peptides, DNA and RNA).

The lipid or lipid-forming materials used to carry out the invention include all known materials for liposome or vesicle formation. Examples of useful materials include combinations of phospholipid molecules and cholesterol. Example phospholipid molecules include Phosphatidic acid (phosphatidate) (PA), Phosphatidylethanolamine (cephalin) (PE), Phosphatidylcholine (lecithin) (PC), Phosphatidylserine (PS), Phosphoinositides: Phosphatidylinositol (PI), Phosphatidylinositol phosphate (PIP), Phosphatidylinositol bisphosphate (PIP2) and Phosphatidylinositol triphosphate (PIP3). Example Phosphosphingolipids include Ceramide phosphorylcholine (Sphingomyelin) (SPH), Ceramide phosphorylethanolamine (Sphingomyelin) (Cer-PE) And Ceramide phosphoryllipid. Particularly preferred are combinations of dimyristoylphosphatidylcholine, cholesterol, and dicetylphosphate. These materials may be provided in a solvent that dissolves the lipid or lipid-forming materials.

Vesicle-containing compositions can be produced using the described methods, having mean diameters from 1 µm to 200 µm, e.g., 1 µm, 2 µm, 4 µm, 6 µm, 8 µm, 10 µm, 12 µm, 14 µm, 16 µm, 18 µm, 20 µm, 22 µm, 24 µm, 26 µm, 28 µm, 30 µm, 32 µm, 34 µm, 36 µm, 38 µm, 40 µm, 42 µm, 44 µm, 46 µm, 48 µm, 50 µm, 75 µm, 100 µm, 125 µm, 150 µm, 175 µm and 200 µm, and a size distribution of 5 to 50%, 10 to 30% or 15 to 20%. The methods described here can be used to provide vesicles for applications in on-demand drug encapsulation and delivery.

Methods may be used to remove oil caps from vesicles, e.g., subjecting vesicles to a high shear flow forces. Upon removal, the vesicles sink in a solution with physiological electrolyte concentrations, and the oil drops float to the surface and are easily removed, if desired.

Drug Delivery Systems

Therapeutic agents such as proteins/peptides, nucleic acids, anticarcinogens, and other drugs have the drawbacks of low bioavailability, rapid clearance, and high toxicity. Therefore, there is a great demand to develop delivery methods and carriers, which will bring a more efficient delivery for therapeutics.

Drug delivery systems (DDS) are capable of being designed to increase the bioavailability of drugs, control drug delivery and maintain the drug intact transport to the site of action while avoiding the non-diseased host tissues. Briefly, in a suitable dosage and mode of administration, using the smallest dose to achieve the best therapeutic effect is the research objective of DDS.

As main components of cellular membranes, phospholipids have excellent biocompatibility. In addition, phospholipids are known for their amphiphilic structures. The amphiphilicity confers phospholipids with self-assembly, emulsifying and wetting characteristics. When introduced into an aqueous milieu, phospholipid self-assembly generates different supermolecular structures, which are dependent on their specific properties and conditions. For example, phospholipids have a propensity to form liposomes, which can be employed as the drug carriers. Phospholipids have good emulsifying properties, which can stabilize emulsions. In addition, phospholipids act as surface-active wetting agents, which can coat the surface of crystals to enhance the hydrophilicity of hydrophobic drugs. These properties are consistent with DDS design.

Phospholipids are molecules in which hydrophilic head group and hydrophobic acyl chains are linked to an alcohol. Variation in head groups, aliphatic chains and alcohols leads to the existence of a wide variety of phospholipids. In addition, different sources of phospholipids also enhance the species of phospholipids. Various phospholipids, such as soybean phosphatidylcholine, egg phosphatidylcholine, or synthetic phosphatidylcholine, as well as hydrogenated phosphatidylcholine, are commonly used in different types of formulations.

Phospholipids

Phospholipids are lipids containing phosphorus, a polar potion and non-polar potion in their structures. According to the alcohols contained in the phospholipids, they can be divided into glycerophospholipids and sphingomyelins.

Glycerophospholipids which are the main phospholipids in eukaryotic cells, refer to the phospholipids in which glycerol is the backbone. All naturally occurring glycerophospholipids possess α-structure and L-configuration. The chemical structures of glycerophospholipids can be classified by the head group, the length and the saturation of hydrophobic side chains, the type of bonding between the aliphatic moieties and glycerol backbone, and the number of aliphatic chains. Variation in the head group leads to different glycerophospholipids, such as phosphatidylcholine (PC), phosphatidylethanolamine (PE), phosphatidylserine (PS), phosphatidic acid (PA), phosphatidylinositol (PI), phosphatidylglycerol (PG) cardiolipin (CL). The length of the apolar moieties leads to different glycerophospholipids, e.g., dipalmitoyl, dimyristoyl, distearoyl PC. The saturation of aliphatic groups characterizes different glycerophospholipids, such as dioleoyl, distearoyl PC. The type of bonding (ester or ether) between aliphatic chains and glycerol determines different glycerophospholipids, such as plasmalogen. The number of aliphatic chains is different, for example, lysophospholipids have only one acyl group at the glycerol backbone.

Sphingomyelins are an important component of animal cell membranes. Although PC and SM are very similar in molecular structure, they have some differences. 1) The backbone of SM is a sphingosine, while the backbone of PC is a glycerol. 2) Each SM molecule averagely contains 0.1-0.35 cis-double bonds in amide-linked acyl chains, and PC contains 1.1-1.5 cis-double bonds. The saturation of hydrophobic regions of SMs is higher than that of PCs. 3) The typical acyl lengths of the naturally occurring SMs are usually more than 20, while the paraffin residues of sphingosine are relatively shorter. The SMs are asymmetric molecules. In contrast, PCs typically contain moderate lengths of the acyl chains, and the lengths of two chains are approximately equal, so the PCs are symmetric molecules. 4) SMs are capable of forming intermolecular and intramolecular hydrogen bonds, so the SM and PC bilayer have a significant difference in the macroscopic properties. 5) The range of phase transition temperature (Tc) of all naturally occurring SMs is 30-45° C., which is above the natural PCs. 6) Numerous observations have shown that SM and cholesterol have a very strong interaction, for example, compared with the non-saturated PC/cholesterol bilayer, SM/cholesterol bilayer has higher compressibility, and lower permeability to water. The reason for this phenomenon is that higher saturation of the acyl chain of SM leads to stronger interaction with steroid nucleus.

Natural Phospholipids

Phospholipids are widely distributed in animals and plants, and the main sources include vegetable oils (e.g., soybean, cotton seed, corn, sunflower and rapeseed) and animal tissues (e.g. egg yolk and bovine brain). In terms of production, egg yolk and soybean are common sources for phospholipids. However, soybean and egg yolk have differences in the contents and species of phospholipids, for example: 1) egg yolk lecithin contains a higher amount of PC; 2) phospholipids in egg yolk exist as long chain polyunsaturated fatty acids of n-6 and n-3 series, primarily arachidonic acid (AA) and docosahexaenoic acid (DHA), which are absent in soybean lecithins; 3) animal lecithins characteristically have SM; 4) the saturation level of egg yolk lecithins is higher than that of soybean lecithins, so their oxidative stability is better than that of soybean lecithins; 5) for egg yolk phospholipids, saturated fatty acid is usually at sn-1 position, and unsaturated fatty acid is at sn-2 position, while for soybean lecithin, sn-1 and sn-2 position can be both unsaturated fatty acids. Dilinoleoylphosphatidylcholine (DLPC) is the main component of soybean phosphatidylcholine (SPC).

Phospholipids isolated from plants and animals can be purified to different levels, including food and pharmaceutical grade. For example, lipoid E80 can contain PC, PE, lysophosphatidylcholine (LPC), lysophosphatidylethanolamine (LPE), SM and trace amounts of triglycerides, cholesterol, fatty acid, d, L-α-vitamin E and water.

Synthetic Phospholipids

The synthesis of phospholipids can be divided into semi-synthesis and total synthesis. Semi-synthesis of glycerophospholipids refers to the changing of head, tail groups or both on the basis of natural phospholipids. Total synthesis of glycerophospholipids involves the formation of ester or ether bonds linking apolar moieties to glycerol backbone, and the attachment of polar head group.

Artificial Antigen Presenting Cells

The vesicles produced according to the disclosed methods can be as artificial antigen presenting cells (aAPCs).

Immunotherapy through dendritic cell (DC) vaccination or adoptive cell transfer holds a great therapeutic potential for diseases that can be controlled using the body's own immune system, such as cancer or auto-immune diseases. Cell-based approaches to elicit the desired cellular and humoral immune responses are often hampered to by the complex and unpredictable nature of the immune system. An alternative to cellular-based immunotherapy has been the development of acellular, artificial antigen-presenting cells (aAPCs), of which the exact composition can be tightly controlled. Artificial APCs have found their way in vaccination and ACT.

Figure 8:
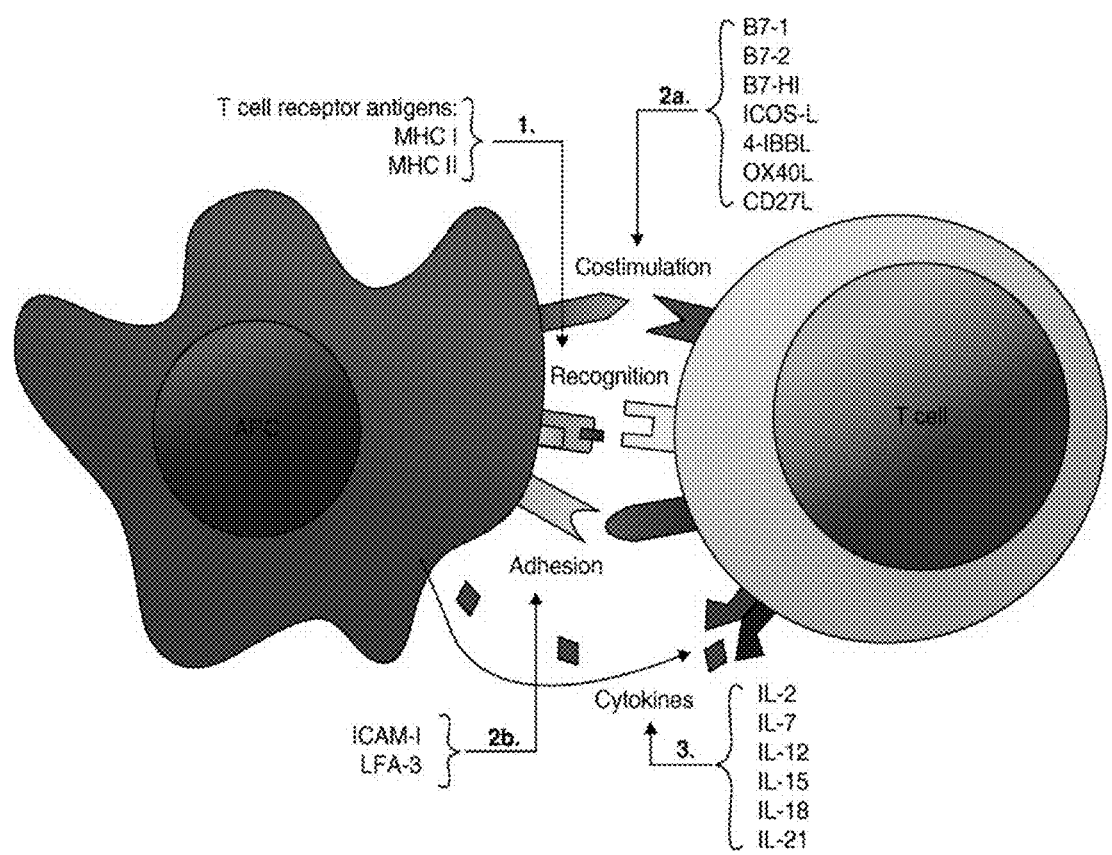
FIG. 8. Schematic of signal classes presented by an antigen-presenting cell (APC). Three signals are essential for optimal T cell stimulation: 1. Recognition signals that ligate the T cell antigen receptor, pMHC complexes or antibodies cross-linking the T cell receptor (TCR), 2. Costimulatory molecules of the CD80/86 or TNF family and adhesive molecules that strengthen interactions between cells, 3. Cytokines secreted by APC or other immune cells that bind to receptors on the T cell surface.

Antigen presentation by natural APCs can lead to variety of T cell responses, depending on which signals are transmitted. Therefore, control over the signals incorporated into artificial antigen-presenting cells improves control over the therapeutic outcome. The information that is transmitted by an APC to activate, expand and differentiate a naïve T cell is classically divided into three signals, as illustrated in FIG. 8.

The first signal, recognition, takes place when a T cell receptor (TCR) on a T cell recognizes a peptide-MHC (pMHC) complex on an APC surface. For artificial antigen presentation, either an pMHC class I (for expanding CD4+ T cells) or pMHC II (for expanding CD8+ T cells) can be used as recognition signal. Often, an MHC I/II non-specific antibody, anti-CD3, is used as an alternative recognition signal on surface of aAPCs. Antibodies are more easily produced in large quantities and only one aAPC is required for the activation and expansion of a diverse repertoire of T cells.

Costimulation through the interaction of CD80/86 receptors on the APC and CD28 on T cells is known to enhance the strength of the antigen-specific T cell response. Many aAPCs therefore present either CD80/86 or anti-CD28 on their surface as a second signal, although stimulation with aCD28 may only lead to T cell proliferation but not differentiation. In addition to costimulatory ligands, adhesive interactions though ICAM-1 on the APC surface with LFA-1 on T cells may serve to enhance affinity and prolong APC:T cell interaction. As such, anti-LFA-1 has been used in artificial APC systems.

An important factor in the rapid expansion and differentiation of T cells comes from cytokines, which are either released by the APC or by neighboring activated T cells. Cytokines are extensively used for the ex vivo culture of T cells (in adoptive transfer for example) or for direct in vivo administration as a form of immunotherapy. Cytokine release has only recently been mimicked in local delivery strategies, mainly in biodegradable PLGA particles or anchored to liposomes through an Fc-fragment.

T helper cells ($T_H$ cells) assist other white blood cells in immunologic processes, including maturation of B cells into plasma cells and memory B cells, and activation of cytotoxic T cells and macrophages. These cells are also known as CD4$^+$ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_FH$, which secrete different cytokines to facilitate different types of immune responses. Signaling from the APC directs T cells into particular subtypes.

Cytotoxic T cells ($T_C$ cells, or CTLs) destroy virus-infected cells and tumor cells, and are also implicated in transplant rejection. These cells are also known as CD8$^+$ T cells since they express the CD8 glycoprotein at their surfaces. These cells recognize their targets by binding to antigen associated with MHC class I molecules, which are present on the surface of all nucleated cells. Through IL-10, adenosine, and other molecules secreted by regulatory T cells, the CD8$^+$ cells can be inactivated to an anergic state, which prevents autoimmune diseases.

Natural killer T cells (NKT cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both $T_H$ and $T_C$ cells (i.e., cytokine production and release of cytolytic/cell killing molecules). They are also able to recognize and eliminate some tumor cells and cells infected with herpes viruses.

The modular, systematic description of T cell stimulation is compatible with methods of artificial antigen presentation. The type of T cell response can be precisely tuned, depending on the signals provided by the aAPC. Controlled display of information to T cells not only helps to increase our fundamental understanding of the nature of T cell activation, but also provides a basis for well-defined immunotherapies.

The methods disclosed herein are used to produce vesicles that contain surface stimulatory molecules that are capable of stimulating an immune response. Peptide-MHC (pMHC) complexes and costimulatory molecules are incorporated into vesicles to yield artificial APCs.

Long-Term Protein and/or Drug Storage

Methods for long-term storage of proteins or drugs in the double emulsion templates are also disclosed. Double emulsions comprising one or more proteins and/or drugs are stored in an isotonic solution with a small amount of surfactant and are stable for over a year. The procedure is ideally suited for work with labile and highly reactive molecules. Because the biological activity of encapsulated molecules is largely maintained during the preparation, this technique is useful in liposome-based drug delivery schemes, carried out by forming protein or drug-containing vesicles upon demand.

Example 1

Formation of a Water-Oil-Water Double Emulsion and Vesicles

Figure 1:
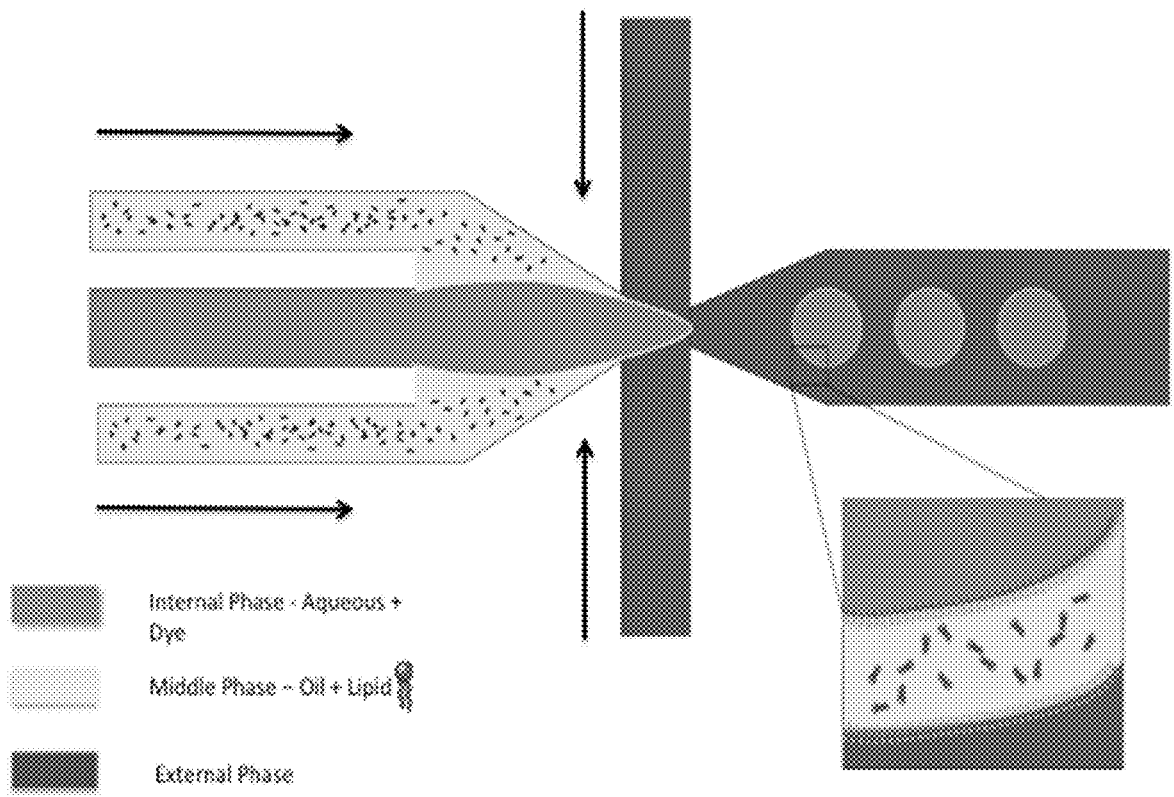
FIG. 1. A) Schematic illustration of the production of double emulsions templates through co-laminar flow of oil and internal aqueous phases. B) Optical microscope image of double emulsion production.
Figure 1:
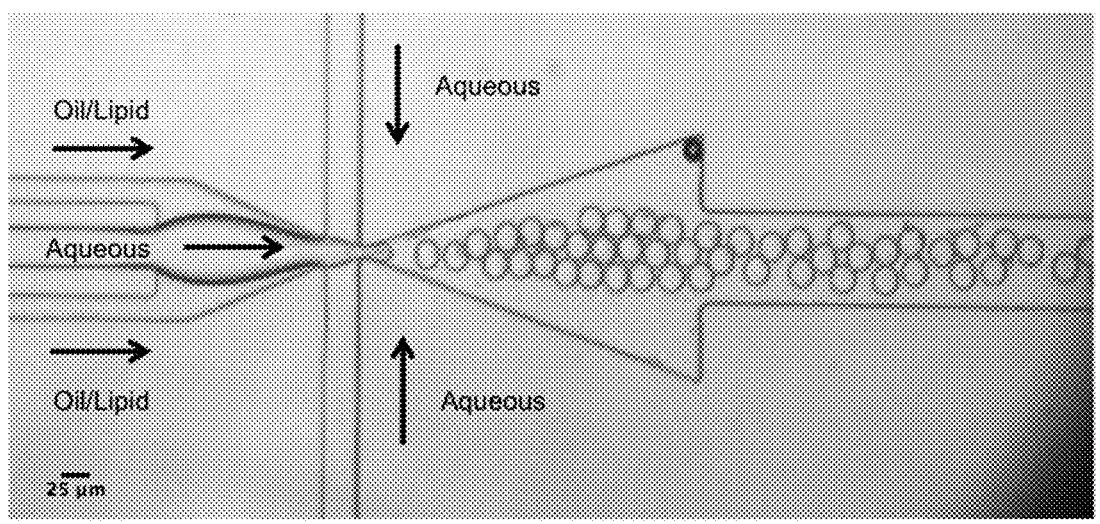
Figure 2:
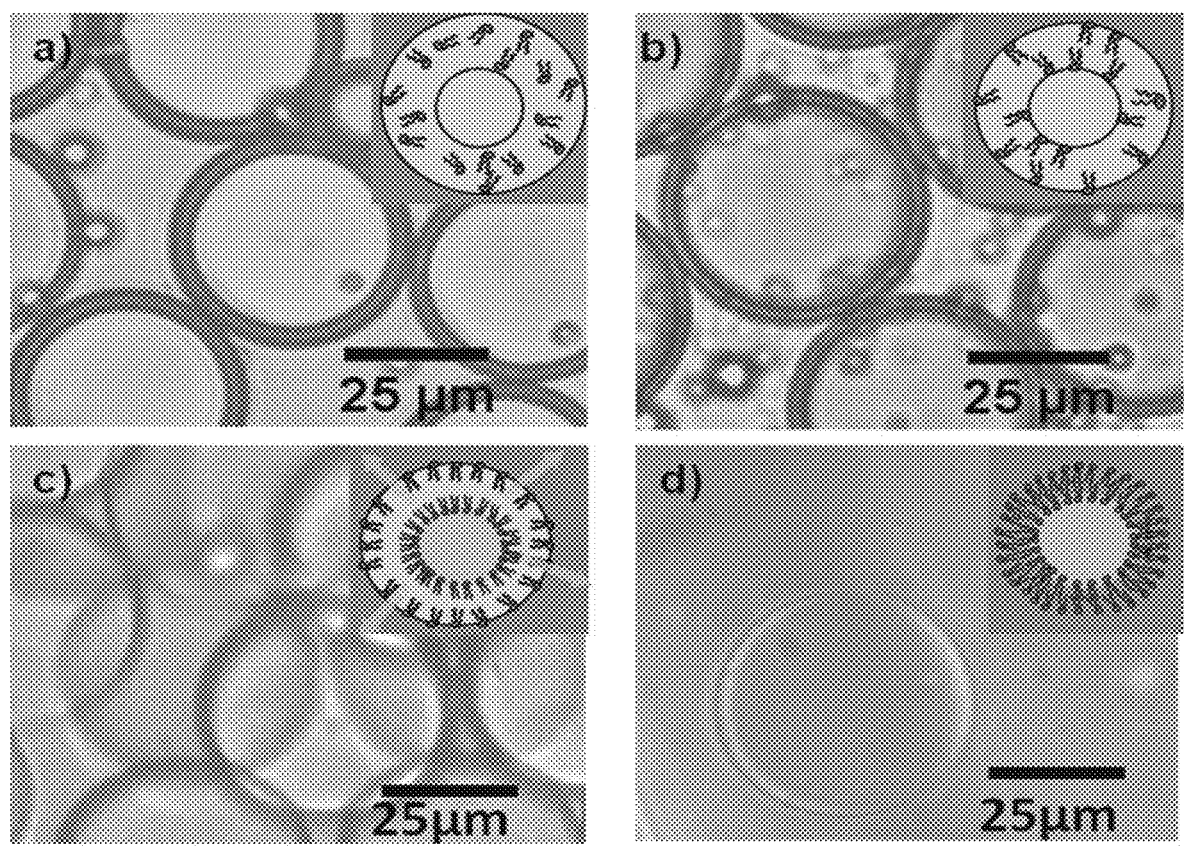
FIG. 2. Time-lapse images of solvent extraction process at 0, 5, 10, and 15 hours (a-d) post-production. Solvent extraction is indicated by a reduction in thickness of the middle layer. As oil is removed, lipid molecules are forced to assemble into a bilayer at the water interface (S. Y. Teh and A. P. Lee, "Microfluidic double emulsions for the formulation of lipid vesicles and the controlled encapsulation of cells," presented at the 13th International Conference on Miniaturized Systems for Chemistry and Life Sciences (MicroTAS 2009), Jeju, Korea, 2009). The inset schematic diagrams in panels a-d depict the lipid bilayer, which forms upon removal of oil.

We begin by forming a thin shell W/O/W double emulsion within a microfluidic device (FIG. 1). The double emulsions consist of an internal aqueous compartment with 5% Pluronic F68 (Sigma-Aldrich) and a 250 mM sucrose solution, surrounded by a thin oil layer with 10 mg/ml 1,2-dioleoyl-sn-glycero-3-phosphocholine (DOPC, Avanti) and 5 mg/ml cholesterol (Research Chemicals Ltd). These double emulsions can be stored for at least a year, without any morphological changes or degradation.

Figure 6:
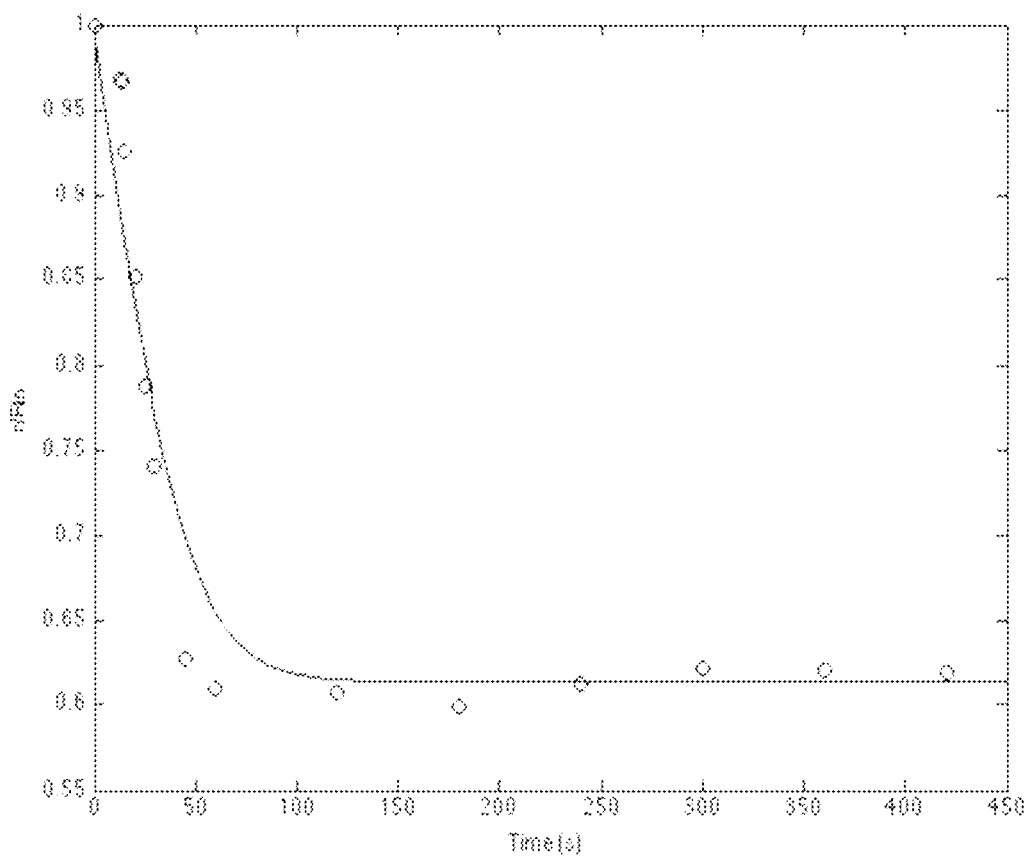
FIG. 6. Decrease in vesicle radius in response to osmotic pressure shock. Vesicle radius is normalized to the initial radius (Rin). (T. Yoshitani and M. Yamazaki, "Water permeability of lipid membranes of GUVs and its dependence on actin cytoskeletons inside the GUVs," in Micro-Nano-Mechatronics and Human Science, 2008. MHS 2008. International Symposium on, 2008, pp. 130-134).

Upon transfer to an electrolytic solution (typically 1×PBS or 250 mOsM NaCl) without any stabilizing surfactant (Pluronic F68), the double emulsions undergo a morphological transformation whereby they become vesicles. It is common knowledge that ionic solutions tend to have higher surface tension (or interfacial tensions with oils) than does pure water, a phenomenon known as the specific ion, or Hofmeister, effect (E. R. A. Lima et al. 2013 *Brazilian Journal of Chemical Engineering* 30: 55-62; A. P. dos Santos et al. 2010 *Langmuir* 26: 10778-10783; A. P. dos Santos and Y. Levin 2013 *Faraday Discussions* 160: 75-87). The specific ion effect increases hydrophobic interactions, and we suspect the increased interfacial tension forces the oil phase to adopt a more energetically favorable morphology by reducing its surface area, causing it to accumulate at one region of the double emulsion in order to reduce the exposed surface area. The local concentration of lipids in the thinning portion of the middle layer promotes a depletion effect (R. C. Hayward et al. 2006 *Langmuir* 22: 4457-4461), whereby the hydrophobic lipid tails attract to each other and push away the smaller solvent molecules. The result is that the oil phase ultimately undergoes a process known as "dewetting" (FIGS. 3 & 4), forming a vesicle with a small oil cap. By increasing the molarity of the external solution and measuring the rate of vesicle shrinkage, we were able to estimate the permeability of the membrane to water at 53.6±3.4 um/s (FIG. 6), well within the range of 15-150 um/s as reported in the literature for DOPC bilayers (T. Yoshitani and M. Yamazaki, "Water permeability of lipid membranes of GUVs and its dependence on actin cytoskeletons inside the GUVs," in Micro-NanoMechatronics and Human Science, 2008. MHS 2008. International Symposium on, 2008, pp. 130-134).

Oil caps can be removed from the vesicles, e.g., subjecting the vesicles to a high shear flow forces. Upon removal, the vesicles sink in a solution with physiological electrolyte concentrations, and the oil drops float to the surface and are easily removed, if needed. In some embodiments, the process to remove the oil caps is optimized, although it may not be necessary for most applications, and they can become very small when exposed to different ions (<5% total surface area, FIG. 6). Once the vesicles are formed, they can survive in solution for about 1-3 days.

Example 2

Formation of Artificial Antigen Presenting Cells

We begin by forming a thin shell W/O/W double emulsion within a microfluidic device (FIG. 1). The double emulsions consist of an internal aqueous compartment with 5% Pluronic F68 (Sigma-Aldrich) and a 250 mM sucrose solution, surrounded by a thin oil layer with 10 mg/ml 1,2-dioleoyl-sn-glycero-3-phosphocholine (DOPC, Avanti) and 5 mg/ml cholesterol (Research Chemicals Ltd). Also contained within the thin oil layer are peptide-MHC (pMHC) complexes and costimulatory molecules. These double emulsions can be stored for at least a year, without any morphological changes or degradation. Upon transfer to an electrolytic solution (typically 1×PBS or 250 mOsM NaCl) without any stabilizing surfactant (Pluronic F68), the double emulsions undergo a morphological transformation whereby they become vesicles that contain the peptide-MHC (pMHC) complexes and costimulatory molecules within the lipid bilayer.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A water-in-oil-in-water (W/O/W) double emulsion comprising a first water phase, an oil phase and a second water phase, wherein the oil phase comprises a non-volatile oil and lipid molecules dissolved in the non-volatile oil, wherein the lipid molecules are not assembled in a bilayer, and wherein the W/O/W double emulsion is in an isotonic solution.

2. The W/O/W double emulsion according to claim 1, wherein the isotonic solution comprises a surfactant.

3. The W/O/W double emulsion according to claim 2, wherein the surfactant is a nonionic surfactant.

4. The W/O/W double emulsion according to claim 2, wherein the surfactant is an amphoteric surfactant.

5. The W/O/W double emulsion according to claim 1, wherein the lipid is a nonpolar lipid.

6. The W/O/W double emulsion according to claim 1, wherein the lipid is a polar lipid.

7. The W/O/W double emulsion according to claim 6, wherein the polar lipid is a phospholipid.

8. The W/O/W double emulsion according to claim 6, wherein the phospholipid is a synthetic phospholipid.

9. The W/O/W double emulsion according to claim 7, wherein the phospholipid is selected from the group consisting of phosphatidic acid (phosphatidate) (PA), phosphatidylethanolamine (cephalin) (PE), phosphatidylcholine (lecithin) (PC), phosphatidylserine (PS), phosphatidylinositol (PI), phosphatidylinositol phosphate (PIP), phosphatidylinositol bisphosphate (PIP2), phosphatidylinositol triphosphate (PIP3), dimyristoylphosphatidylcholine, ceramide phosphorylcholine (Sphingomyelin) (SPH), ceramide phosphorylethanolamine (Sphingomyelin) (Cer-PE), ceramide phosphoryllipid and 1,2-dioleoyl-sn-glycero-3-phosphocholine (DOPC).

10. The W/O/W double emulsion according to claim 1, further comprising an agent selected from the group consisting of a drug, a fluorescent molecule, an amino acid, a protein, a peptide, a nucleic acid, a DNA molecule or an RNA molecule.

11. A method of making a water-in-oil-in-water (W/O/W) double emulsion according to claim 1, comprising:
    forming a water-in-oil-in-water (W/O/W) double emulsion, wherein the W/O/W double emulsion comprises a first water phase, an oil phase comprising a non-volatile oil and a lipid and a second water phase, wherein the lipid molecules are not assembled in a bilayer; and
    storing the W/O/W double emulsion in an isotonic solution.

12. A method of storing a protein comprising making a water-in-oil-in-water (W/O/W) double emulsion according to claim 10, wherein the W/O/W double emulsion comprises the protein, and wherein the W/O/W double emulsion is configured to be able to be stably stored for up to one year or more.

13. An aqueous solution comprising a vesicle, wherein the vesicle comprises an internal aqueous phase and a unilamellar lipid bilayer that envelops the internal aqueous phase, wherein the unilamellar lipid bilayer has an oil cap disposed on the exterior of the unilamellar lipid bilayer, wherein the oil cap consists essentially of an oil.

14. A water-in-oil-in-water (W/O/W) double emulsion comprising a first water phase, an oil phase and a second water phase, wherein the oil phase consists of a non-volatile oil, cholesterol and lipid molecules, wherein the lipid molecules are not assembled in a bilayer, and wherein the W/O/W double emulsion is in an isotonic solution.

15. The water-in-oil-in water double emulsion according to claim 1, wherein the non-volatile oil comprises a fatty acid.

\* \* \* \* \*